US009023094B2

(12) United States Patent
Tieu et al.

(10) Patent No.: US 9,023,094 B2
(45) Date of Patent: May 5, 2015

(54) SELF-EXPANDING PROSTHESIS (75) Inventors: Tai D. Tieu, Fountain Valley, CA (US); Joseph Gulachenski, Trabuco Canyon, CA (US)

(73) Assignee: MicroVention, Inc., Tustin, CA (US)

( * ) Notice: Subject to any disclaimer, the term of this patent is extended or adjusted under 35 U.S.C. 154(b) by 320 days.

(21) Appl. No.: 12/146,252

(22) Filed: Jun. 25, 2008

(65) Prior Publication Data

US 2008/0319525 A1     Dec. 25, 2008

Related U.S. Application Data (60) Provisional application No. 60/946,101, filed on Jun. 25, 2007.

(51) Int. Cl.
*A61F 2/06* (2013.01)
*A61F 2/86* (2013.01)
*A61F 2/95* (2013.01)
*A61F 2/82* (2013.01)

(52) U.S. Cl.
CPC ... *A61F 2/86* (2013.01); *A61F 2/95* (2013.01); *A61F 2002/823* (2013.01); *A61F 2210/0014* (2013.01); *A61F 2210/0033* (2013.01)

(58) Field of Classification Search
USPC ............ 623/1.11, 1.19; 606/27–41, 108, 191, 606/194, 195, 200
See application file for complete search history.

(56) References Cited

U.S. PATENT DOCUMENTS

| | | | |
|---|---|---|---|
| 3,842,441 A | 10/1974 | Kaiser | |
| 3,868,956 A | 3/1975 | Alfidi et al. | |
| 4,130,904 A | 12/1978 | Whalen | |
| 4,140,126 A | 2/1979 | Choudhury | |
| 4,286,341 A | 9/1981 | Greer et al. | |
| 4,503,569 A * | 3/1985 | Dotter | 623/1.19 |
| 4,512,338 A | 4/1985 | Balko et al. | |
| 4,553,545 A | 11/1985 | Maass et al. | |
| 4,562,596 A | 1/1986 | Kornberg | |
| 4,577,631 A | 3/1986 | Kreamer | |
| 4,629,458 A | 12/1986 | Pinchuk | |
| 4,655,771 A | 4/1987 | Wallsten | |
| 4,655,918 A | 4/1987 | Eertink | |
| 4,663,358 A | 5/1987 | Hyon et al. | |
| 4,670,286 A | 6/1987 | Nyilas et al. | |

(Continued)

FOREIGN PATENT DOCUMENTS

| | | |
|---|---|---|
| AU | 2002316320 B2 | 6/2009 |
| AU | 2010249161 A1 | 12/2010 |

(Continued)

OTHER PUBLICATIONS

World International Patent Organization—ISA/US, Search Report and Written Opinion in International Patent Application No. PCT/US2008/068210 issued Oct. 3, 2008, 5 pages.

(Continued)

*Primary Examiner* — Katherine M Shi

(74) *Attorney, Agent, or Firm* — Inskeep IP Group, Inc.

(57) ABSTRACT

In one preferred embodiment, a prosthesis is provided that can be selectively expanded by increasing the temperature of the prosthesis within the patient. The prosthesis is composed of a shape memory material that expands when heated to a temperature greater than an average body temperature, allowing the user to selectively heat and therefore expand the prosthesis at a desired location.

9 Claims, 6 Drawing Sheets

(56) References Cited

U.S. PATENT DOCUMENTS

| | | |
|---|---|---|
| 4,681,110 A | 7/1987 | Wiktor |
| 4,718,907 A | 1/1988 | Karwoski et al. |
| 4,723,549 A | 2/1988 | Wholey et al. |
| 4,733,665 A | 3/1988 | Palmaz |
| 4,734,097 A | 3/1988 | Tanabe et al. |
| 4,740,207 A | 4/1988 | Kreamer |
| 4,768,507 A | 9/1988 | Fischell et al. |
| 4,795,458 A | 1/1989 | Regan |
| 4,798,606 A | 1/1989 | Pinchuk |
| 4,800,882 A | 1/1989 | Gianturco |
| 4,813,925 A | 3/1989 | Anderson, Jr. et al. |
| 4,820,298 A | 4/1989 | Leveen et al. |
| 4,852,568 A | 8/1989 | Kensey |
| 4,856,516 A | 8/1989 | Hillstead |
| 4,877,030 A | 10/1989 | Beck et al. |
| 4,878,906 A | 11/1989 | Lindemann et al. |
| 4,898,702 A | 2/1990 | Elkins et al. |
| 4,932,419 A | 6/1990 | de Toledo |
| 4,941,870 A | 7/1990 | Okada et al. |
| 4,950,258 A | 8/1990 | Kawai et al. |
| 4,954,126 A | 9/1990 | Wallstéen |
| 4,969,890 A | 11/1990 | Sugita et al. |
| 4,990,155 A | 2/1991 | Wilkoff |
| 4,990,582 A | 2/1991 | Salamone |
| 4,994,069 A | 2/1991 | Ritchart et al. |
| 5,015,253 A | 5/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,037,391 A | 8/1991 | Hammerslag et al. |
| 5,041,126 A | 8/1991 | Gianturco |
| 5,041,292 A | 8/1991 | Feijen |
| 5,061,275 A | 10/1991 | Wallstéen et al. |
| 5,071,407 A | 12/1991 | Termin et al. |
| 5,078,726 A | 1/1992 | Kreamer |
| 5,084,065 A | 1/1992 | Weldon et al. |
| 5,104,404 A | 4/1992 | Wolff |
| 5,108,407 A | 4/1992 | Geremia et al. |
| 5,108,417 A | 4/1992 | Sawyer |
| 5,108,421 A | 4/1992 | Fowler |
| 5,116,365 A | 5/1992 | Hillstead |
| 5,122,136 A | 6/1992 | Guglielmi et al. |
| 5,133,731 A | 7/1992 | Butler et al. |
| 5,133,732 A | 7/1992 | Wiktor |
| 5,135,536 A | 8/1992 | Hillstead |
| 5,141,502 A | 8/1992 | Macaluso, Jr. |
| 5,146,355 A | 9/1992 | Prince et al. |
| 5,147,370 A | 9/1992 | McNamara et al. |
| 5,151,105 A | 9/1992 | Kwan-Gett |
| 5,158,548 A | 10/1992 | Lau et al. |
| 5,162,430 A | 11/1992 | Rhee et al. |
| 5,163,952 A | 11/1992 | Froix |
| 5,171,262 A | 12/1992 | MacGregor |
| 5,176,625 A | 1/1993 | Brisson |
| 5,183,085 A | 2/1993 | Timmermans |
| 5,192,297 A | 3/1993 | Hull |
| 5,197,978 A | 3/1993 | Hess |
| 5,217,484 A | 6/1993 | Marks |
| 5,222,969 A | 6/1993 | Gillis |
| 5,226,911 A | 7/1993 | Chee et al. |
| 5,234,437 A | 8/1993 | Sepetka |
| 5,234,456 A | 8/1993 | Silvestrini |
| 5,250,071 A | 10/1993 | Palermo |
| 5,256,146 A | 10/1993 | Ensminger et al. |
| 5,258,042 A | 11/1993 | Mehta |
| 5,261,916 A | 11/1993 | Engelson |
| 5,263,964 A | 11/1993 | Purdy |
| 5,304,195 A | 4/1994 | Twyford, Jr. et al. |
| 5,304,200 A | 4/1994 | Spaulding |
| 5,306,294 A | 4/1994 | Winston et al. |
| 5,308,889 A | 5/1994 | Rhee et al. |
| 5,312,415 A | 5/1994 | Palermo |
| 5,314,444 A | 5/1994 | Gianturco |
| 5,314,472 A | 5/1994 | Fontaine |
| 5,342,300 A | 8/1994 | Stefanadis et al. |
| 5,342,387 A | 8/1994 | Summers |
| 5,350,397 A | 9/1994 | Palermo et al. |
| 5,354,295 A | 10/1994 | Guglielmi et al. |
| 5,382,259 A | 1/1995 | Phelps et al. |
| 5,382,260 A | 1/1995 | Dormandy, Jr. et al. |
| 5,383,887 A | 1/1995 | Nadal |
| 5,383,926 A | 1/1995 | Lock et al. |
| RE34,866 E | 2/1995 | Kensey et al. |
| 5,389,106 A | 2/1995 | Tower |
| 5,395,390 A | 3/1995 | Simon et al. |
| 5,405,377 A | 4/1995 | Cragg |
| 5,410,016 A | 4/1995 | Hubbell et al. |
| 5,415,664 A | 5/1995 | Pinchuk |
| 5,417,708 A | 5/1995 | Hall et al. |
| D359,802 S | 6/1995 | Fontaine |
| 5,433,723 A | 7/1995 | Lindenberg et al. |
| 5,441,516 A | 8/1995 | Wang et al. |
| 5,464,395 A | 11/1995 | Faxon et al. |
| 5,464,449 A | 11/1995 | Ryan et al. |
| 5,476,472 A | 12/1995 | Dormandy, Jr. et al. |
| 5,476,505 A | 12/1995 | Limon |
| 5,480,423 A | 1/1996 | Ravenscroft et al. |
| 5,484,449 A | 1/1996 | Amundson et al. |
| 5,500,013 A | 3/1996 | Buscemi et al. |
| 5,514,154 A | 5/1996 | Lau et al. |
| 5,514,176 A | 5/1996 | Bosley, Jr. |
| 5,514,379 A | 5/1996 | Weissleder et al. |
| 5,514,380 A | 5/1996 | Song et al. |
| 5,522,822 A | 6/1996 | Phelps et al. |
| 5,522,836 A | 6/1996 | Palermo |
| 5,523,092 A | 6/1996 | Hanson et al. |
| 5,536,274 A | 7/1996 | Neuss |
| 5,540,701 A | 7/1996 | Sharkey et al. |
| 5,540,713 A | 7/1996 | Schnepp-Pesch et al. |
| 5,554,181 A | 9/1996 | Das |
| 5,558,633 A | 9/1996 | Phipps et al. |
| 5,562,641 A | 10/1996 | Flomenblit et al. |
| 5,571,181 A | 11/1996 | Li |
| 5,578,074 A | 11/1996 | Mirigian |
| 5,582,619 A | 12/1996 | Ken |
| 5,591,599 A | 1/1997 | Chang et al. |
| 5,601,593 A | 2/1997 | Freitag |
| 5,601,600 A | 2/1997 | Ton |
| 5,603,694 A | 2/1997 | Brown et al. |
| 5,607,445 A | 3/1997 | Summers |
| 5,609,627 A | 3/1997 | Goicoechea et al. |
| 5,609,628 A | 3/1997 | Keranen |
| 5,609,629 A | 3/1997 | Fearnot et al. |
| 5,613,981 A | 3/1997 | Boyle et al. |
| 5,624,461 A | 4/1997 | Mariant |
| 5,630,829 A | 5/1997 | Lauterjung |
| 5,639,277 A | 6/1997 | Mariant et al. |
| 5,645,558 A | 7/1997 | Horton |
| 5,658,308 A | 8/1997 | Snyder |
| 5,662,621 A | 9/1997 | Lafontaine |
| 5,674,241 A | 10/1997 | Bley et al. |
| 5,674,276 A | 10/1997 | Andersen et al. |
| 5,674,277 A | 10/1997 | Freitag |
| 5,674,295 A | 10/1997 | Ray et al. |
| 5,676,697 A | 10/1997 | McDonald |
| 5,681,344 A | 10/1997 | Kelly |
| 5,690,667 A | 11/1997 | Gia |
| 5,690,671 A | 11/1997 | McGurk et al. |
| 5,693,085 A | 12/1997 | Buirge et al. |
| 5,695,480 A | 12/1997 | Evans et al. |
| 5,702,373 A | 12/1997 | Samson |
| 5,702,418 A | 12/1997 | Ravenscroft |
| 5,707,389 A | 1/1998 | Louw et al. |
| 5,713,907 A | 2/1998 | Hogendijk et al. |
| 5,716,410 A | 2/1998 | Wang et al. |
| 5,718,711 A | 2/1998 | Berenstein et al. |
| 5,725,534 A | 3/1998 | Rasmussen |
| 5,733,294 A | 3/1998 | Forber et al. |
| 5,741,325 A | 4/1998 | Chaikof et al. |
| 5,749,894 A | 5/1998 | Engelson |
| 5,749,918 A | 5/1998 | Hogendijk et al. |
| 5,749,919 A | 5/1998 | Blanc |
| 5,749,922 A | 5/1998 | Slepian et al. |
| 5,750,585 A | 5/1998 | Park et al. |

(56) References Cited

U.S. PATENT DOCUMENTS

| | | |
|---|---|---|
| 5,752,974 A | 5/1998 | Rhee et al. |
| 5,759,161 A | 6/1998 | Ogawa et al. |
| 5,766,160 A | 6/1998 | Samson et al. |
| 5,769,882 A | 6/1998 | Fogarty et al. |
| 5,785,679 A | 7/1998 | Abolfathi et al. |
| 5,785,965 A | 7/1998 | Pratt et al. |
| 5,800,454 A | 9/1998 | Jacobsen et al. |
| 5,814,062 A | 9/1998 | Sepetka et al. |
| 5,823,198 A | 10/1998 | Jones et al. |
| 5,824,053 A | 10/1998 | Khosravi et al. |
| 5,824,059 A | 10/1998 | Wijay |
| 5,830,229 A | 11/1998 | Konya et al. |
| 5,830,230 A | 11/1998 | Berryman et al. |
| 5,843,089 A | 12/1998 | Sahatjian et al. |
| 5,868,778 A | 2/1999 | Gershony et al. |
| 5,891,155 A | 4/1999 | Irie |
| 5,895,391 A | 4/1999 | Farnholtz |
| 5,898,062 A | 4/1999 | Allcock et al. |
| 5,911,161 A | 6/1999 | Harris |
| 5,911,717 A | 6/1999 | Jacobsen et al. |
| 5,911,731 A | 6/1999 | Pham et al. |
| 5,928,260 A | 7/1999 | Chin et al. |
| 5,935,148 A | 8/1999 | Villar et al. |
| 5,941,249 A | 8/1999 | Maynard |
| 5,951,599 A | 9/1999 | McCrory |
| 5,976,152 A | 11/1999 | Regan et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,963 A | 11/1999 | Ryan et al. |
| 5,989,242 A | 11/1999 | Saadat et al. |
| 5,990,237 A | 11/1999 | Bentley et al. |
| 6,015,424 A | 1/2000 | Rosenbluth et al. |
| 6,015,431 A | 1/2000 | Thornton et al. |
| 6,019,779 A | 2/2000 | Thorud et al. |
| 6,033,436 A | 3/2000 | Steinke et al. |
| 6,036,720 A | 3/2000 | Abrams et al. |
| 6,053,940 A | 4/2000 | Wijay |
| 6,059,815 A | 5/2000 | Lee et al. |
| 6,060,534 A | 5/2000 | Ronan et al. |
| 6,063,070 A | 5/2000 | Eder |
| 6,063,111 A | 5/2000 | Hieshima et al. |
| 6,071,292 A | 6/2000 | Makower et al. |
| 6,086,577 A | 7/2000 | Ken et al. |
| 6,090,911 A | 7/2000 | Petka et al. |
| 6,093,199 A | 7/2000 | Brown et al. |
| 6,113,628 A | 9/2000 | Borghi |
| 6,113,629 A | 9/2000 | Ken |
| 6,120,847 A | 9/2000 | Yang et al. |
| 6,123,714 A | 9/2000 | Gia et al. |
| 6,139,564 A | 10/2000 | Teoh |
| 6,140,127 A | 10/2000 | Sprague |
| 6,152,144 A | 11/2000 | Lesh et al. |
| 6,152,943 A | 11/2000 | Sawhney |
| 6,162,244 A | 12/2000 | Braun et al. |
| 6,165,193 A | 12/2000 | Greene, Jr. et al. |
| 6,165,194 A | 12/2000 | Denardo |
| 6,165,201 A | 12/2000 | Sawhney et al. |
| 6,168,592 B1 | 1/2001 | Kupiecki et al. |
| 6,168,615 B1 | 1/2001 | Ken et al. |
| 6,176,240 B1 | 1/2001 | Nikolchev et al. |
| 6,177,095 B1 | 1/2001 | Sawhney et al. |
| 6,183,495 B1 | 2/2001 | Lenker et al. |
| 6,184,266 B1 | 2/2001 | Ronan et al. |
| 6,187,370 B1 | 2/2001 | Dinh et al. |
| 6,190,402 B1 | 2/2001 | Horton et al. |
| 6,193,708 B1 | 2/2001 | Ken et al. |
| 6,201,065 B1 | 3/2001 | Pathak et al. |
| 6,203,779 B1 | 3/2001 | Ricci et al. |
| 6,221,099 B1 | 4/2001 | Andersen et al. |
| 6,224,892 B1 | 5/2001 | Searle |
| 6,231,596 B1 | 5/2001 | Collins |
| 6,231,597 B1 | 5/2001 | Deem et al. |
| 6,238,403 B1 | 5/2001 | Greene, Jr. et al. |
| 6,241,691 B1 | 6/2001 | Ferrera et al. |
| 6,249,952 B1 | 6/2001 | Ding |
| 6,254,628 B1 | 7/2001 | Wallace et al. |
| 6,261,305 B1 | 7/2001 | Marotta et al. |
| 6,264,695 B1 | 7/2001 | Stoy |
| 6,268,161 B1 | 7/2001 | Han et al. |
| 6,273,908 B1 | 8/2001 | Ndondo-Lay |
| 6,280,457 B1 | 8/2001 | Wallace et al. |
| 6,287,333 B1 | 9/2001 | Appling et al. |
| 6,288,829 B1 | 9/2001 | Kimura |
| 6,303,100 B1 | 10/2001 | Ricci et al. |
| 6,309,367 B1 | 10/2001 | Boock |
| 6,325,000 B1 | 12/2001 | Furuta |
| 6,325,789 B1 | 12/2001 | Janzen et al. |
| 6,350,274 B1 | 2/2002 | Li |
| 6,360,129 B1 | 3/2002 | Ley et al. |
| 6,361,558 B1 | 3/2002 | Hieshima et al. |
| 6,364,893 B1 | 4/2002 | Sahatjian et al. |
| 6,383,174 B1 | 5/2002 | Eder |
| 6,398,808 B1 | 6/2002 | Palasis |
| 6,419,686 B1 | 7/2002 | McLeod et al. |
| 6,470,115 B1 | 10/2002 | Yonekubo |
| 6,475,466 B1 | 11/2002 | Ricci et al. |
| 6,485,524 B2 | 11/2002 | Strecker |
| 6,494,907 B1 | 12/2002 | Bulver |
| 6,503,270 B1 | 1/2003 | Richter et al. |
| 6,551,303 B1 | 4/2003 | Van Tassel et al. |
| 6,554,849 B1 | 4/2003 | Jones et al. |
| 6,565,601 B2 | 5/2003 | Wallace et al. |
| 6,569,179 B2 | 5/2003 | Teoh et al. |
| 6,569,190 B2 | 5/2003 | Whalen, II et al. |
| 6,579,305 B1 | 6/2003 | Lashinski |
| 6,582,460 B1 | 6/2003 | Cryer |
| 6,585,757 B1 | 7/2003 | Callol |
| 6,592,614 B2 | 7/2003 | Lenker et al. |
| 6,596,296 B1 | 7/2003 | Nelson et al. |
| 6,605,111 B2 | 8/2003 | Bose et al. |
| 6,605,294 B2 | 8/2003 | Sawhney |
| 6,613,073 B1 | 9/2003 | White et al. |
| 6,613,074 B1 | 9/2003 | Mitelberg et al. |
| 6,632,241 B1 | 10/2003 | Hancock et al. |
| 6,663,607 B2 | 12/2003 | Slaikeu et al. |
| 6,676,692 B2 | 1/2004 | Rabkin et al. |
| 6,676,971 B2 | 1/2004 | Goupil et al. |
| 6,716,445 B2 | 4/2004 | Won et al. |
| 6,723,108 B1 | 4/2004 | Jones et al. |
| 6,730,119 B1 | 5/2004 | Smalling |
| 6,746,468 B1 | 6/2004 | Sepetka et al. |
| 6,786,876 B2 | 9/2004 | Cox |
| 6,802,581 B2 | 10/2004 | Hasseler et al. |
| 6,802,851 B2 | 10/2004 | Jones et al. |
| 6,811,560 B2 | 11/2004 | Jones et al. |
| 6,818,013 B2 | 11/2004 | Mitelberg et al. |
| 6,837,901 B2 | 1/2005 | Rabkin et al. |
| 6,860,899 B1 | 3/2005 | Rivelli, Jr. |
| 6,878,384 B2 | 4/2005 | Cruise et al. |
| 6,881,220 B2 | 4/2005 | Edwin et al. |
| 6,890,339 B2 | 5/2005 | Sahatjian et al. |
| 6,896,696 B2 | 5/2005 | Doran et al. |
| 6,899,730 B1 | 5/2005 | Rivelli, Jr. |
| 6,936,055 B1 | 8/2005 | Ken et al. |
| 6,953,468 B2 | 10/2005 | Jones et al. |
| 6,953,473 B2 | 10/2005 | Porter |
| 7,001,422 B2 | 2/2006 | Escamilla et al. |
| 7,037,330 B1 | 5/2006 | Rivelli, Jr. et al. |
| 7,037,331 B2 | 5/2006 | Mitelberg et al. |
| 7,037,332 B2 | 5/2006 | Kutryk et al. |
| 7,063,719 B2 | 6/2006 | Jansen et al. |
| 7,083,643 B2 | 8/2006 | Whalen, III et al. |
| 7,128,736 B1 | 10/2006 | Abrams et al. |
| 7,156,871 B2 | 1/2007 | Jones et al. |
| 7,195,636 B2 | 3/2007 | Avellanet et al. |
| 7,195,648 B2 | 3/2007 | Jones et al. |
| 7,229,461 B2 | 6/2007 | Chin et al. |
| 7,232,461 B2 | 6/2007 | Ramer |
| 7,241,301 B2 | 7/2007 | Thramann et al. |
| 7,255,710 B2 | 8/2007 | White et al. |
| 7,288,112 B2 | 10/2007 | Denardo et al. |
| 7,303,571 B2 | 12/2007 | Makower et al. |
| 7,306,622 B2 | 12/2007 | Jones et al. |

(56) References Cited

U.S. PATENT DOCUMENTS

| | | | |
|---|---|---|---|
| 7,309,351 B2 | 12/2007 | Escamilla et al. |
| 7,311,726 B2 | 12/2007 | Mitelberg et al. |
| 7,323,005 B2 | 1/2008 | Wallace et al. |
| 7,384,426 B2 | 6/2008 | Wallace et al. |
| 7,410,482 B2 | 8/2008 | Murphy et al. |
| 7,455,753 B2 | 11/2008 | Roth |
| 7,517,361 B1 | 4/2009 | Ravenscroft |
| 7,520,893 B2 | 4/2009 | Rivelli, Jr. |
| 7,569,066 B2 | 8/2009 | Gerberding et al. |
| 7,572,288 B2 | 8/2009 | Cox |
| 7,695,507 B2 | 4/2010 | Rivelli, Jr. et al. |
| 7,713,264 B2 | 5/2010 | Murphy et al. |
| 7,763,011 B2 | 7/2010 | Ortiz et al. |
| 8,075,585 B2 | 12/2011 | Lee et al. |
| 8,252,040 B2 | 8/2012 | Cox |
| 8,562,667 B2 | 10/2013 | Cox |
| 8,715,312 B2 | 5/2014 | Burke et al. |
| 2001/0000188 A1 | 4/2001 | Lenker et al. |
| 2001/0000797 A1 | 5/2001 | Mazzocchi |
| 2001/0003801 A1 | 6/2001 | Strecker |
| 2001/0010015 A1 | 7/2001 | Hijlkema |
| 2001/0012961 A1 | 8/2001 | Deem et al. |
| 2001/0036451 A1 | 11/2001 | Goupil et al. |
| 2001/0047202 A1 | 11/2001 | Slaikeu et al. |
| 2002/0013618 A1 | 1/2002 | Marotta et al. |
| 2002/0026217 A1 | 2/2002 | Baker et al. |
| 2002/0026228 A1 | 2/2002 | Schauerte |
| 2002/0026232 A1 | 2/2002 | Marotta et al. |
| 2002/0049495 A1 | 4/2002 | Kutryk et al. |
| 2002/0052643 A1 | 5/2002 | Wholey |
| 2002/0052648 A1 | 5/2002 | McGuckin, Jr. et al. |
| 2002/0123789 A1 | 9/2002 | Francis et al. |
| 2002/0143349 A1 | 10/2002 | Gifford, III et al. |
| 2002/0169473 A1 | 11/2002 | Sepetka et al. |
| 2002/0169497 A1 | 11/2002 | Wholey et al. |
| 2003/0004531 A1 | 1/2003 | Jones et al. |
| 2003/0018294 A1 | 1/2003 | Cox |
| 2003/0023190 A1 | 1/2003 | Cox |
| 2003/0055451 A1 | 3/2003 | Jones et al. |
| 2003/0120300 A1 | 6/2003 | Porter |
| 2003/0135266 A1* | 7/2003 | Chew et al. ............. 623/1.16 |
| 2003/0135267 A1 | 7/2003 | Solem et al. |
| 2003/0139802 A1 | 7/2003 | Wulfman et al. |
| 2003/0139806 A1 | 7/2003 | Haverkost et al. |
| 2003/0171739 A1 | 9/2003 | Murphy et al. |
| 2003/0195553 A1 | 10/2003 | Wallace et al. |
| 2003/0204246 A1 | 10/2003 | Chu et al. |
| 2004/0034386 A1 | 2/2004 | Fulton et al. |
| 2004/0087998 A1 | 5/2004 | Lee et al. |
| 2004/0093076 A1 | 5/2004 | White et al. |
| 2004/0098027 A1 | 5/2004 | Teoh et al. |
| 2004/0098028 A1 | 5/2004 | Martinez |
| 2004/0106945 A1 | 6/2004 | Thramann et al. |
| 2004/0111112 A1 | 6/2004 | Hoffmann |
| 2004/0158311 A1 | 8/2004 | Berhow et al. |
| 2004/0172056 A1 | 9/2004 | Guterman et al. |
| 2004/0186557 A1 | 9/2004 | Gambale et al. |
| 2004/0186562 A1 | 9/2004 | Cox |
| 2004/0193206 A1 | 9/2004 | Gergerding et al. |
| 2004/0193246 A1 | 9/2004 | Ferrera |
| 2005/0004660 A1 | 1/2005 | Rosenbluth et al. |
| 2005/0033409 A1 | 2/2005 | Burke et al. |
| 2005/0090856 A1 | 4/2005 | Porter |
| 2005/0149164 A1 | 7/2005 | Rivelli, Jr. |
| 2005/0209678 A1 | 9/2005 | Henkes et al. |
| 2006/0069424 A1 | 3/2006 | Acosta et al. |
| 2006/0074447 A2 | 4/2006 | Armstrong |
| 2006/0122685 A1 | 6/2006 | Bonsignore et al. |
| 2006/0206201 A1 | 9/2006 | Garcia et al. |
| 2007/0078480 A1 | 4/2007 | Belenkaya et al. |
| 2007/0083257 A1 | 4/2007 | Pal et al. |
| 2007/0129757 A1 | 6/2007 | Armstrong |
| 2007/0207186 A1 | 9/2007 | Scanlon et al. |
| 2008/0021535 A1 | 1/2008 | Leopold et al. |
| 2008/0033480 A1 | 2/2008 | Hardert |
| 2008/0147100 A1 | 6/2008 | Wallace |
| 2008/0161936 A1 | 7/2008 | Feller et al. |
| 2008/0195136 A1 | 8/2008 | Feller et al. |
| 2008/0221671 A1 | 9/2008 | Chouinard et al. |
| 2008/0281302 A1 | 11/2008 | Murphy et al. |
| 2009/0054965 A1 | 2/2009 | Richard |
| 2009/0149864 A1 | 6/2009 | Porter |
| 2009/0163945 A1 | 6/2009 | Richard et al. |
| 2009/0177264 A1 | 7/2009 | Ravenscroft |
| 2009/0177268 A1 | 7/2009 | Lundkvist et al. |
| 2009/0198315 A1 | 8/2009 | Boudjemline |
| 2009/0228029 A1 | 9/2009 | Lee |
| 2009/0270908 A1 | 10/2009 | Tekulve et al. |
| 2009/0287297 A1 | 11/2009 | Cox |
| 2009/0287300 A1 | 11/2009 | Dave et al. |
| 2009/0306762 A1 | 12/2009 | McCullagh et al. |
| 2009/0312834 A1 | 12/2009 | Wood et al. |
| 2009/0318941 A1 | 12/2009 | Sepetka et al. |
| 2010/0004671 A1 | 1/2010 | Gerberding et al. |
| 2010/0004672 A1 | 1/2010 | Shirley et al. |
| 2010/0152837 A1 | 6/2010 | Lundkvist et al. |
| 2010/0161034 A1 | 6/2010 | Leanna et al. |
| 2010/0191319 A1 | 7/2010 | Lilburn et al. |
| 2010/0204784 A1 | 8/2010 | Molaei et al. |
| 2010/0222804 A1 | 9/2010 | Murphy et al. |
| 2010/0222864 A1 | 9/2010 | Rivelli, Jr. et al. |
| 2012/0310319 A1 | 12/2012 | Tieu et al. |

FOREIGN PATENT DOCUMENTS

| | | |
|---|---|---|
| AU | 2008243176 B2 | 5/2011 |
| CA | 2455464 A1 | 1/2003 |
| CN | ZL200810098576.0 C | 6/2008 |
| EP | 0 272 260 A1 | 6/1988 |
| EP | 0 272 760 A1 | 6/1988 |
| EP | 0 107 055 B2 | 12/1989 |
| EP | 0 441 516 A2 | 8/1991 |
| EP | 0 518 704 A1 | 12/1992 |
| EP | 0518704 A1 | 12/1992 |
| EP | 0 5470530 A1 | 6/1993 |
| EP | 0 627 201 A1 | 12/1994 |
| EP | 0627201 A1 | 12/1994 |
| EP | 0717969 A2 | 6/1996 |
| EP | 0664104 A2 | 9/1998 |
| EP | 0947180 A2 | 10/1999 |
| EP | 1 220 190 A2 | 3/2000 |
| EP | 1 129 666 A1 | 9/2001 |
| EP | 1 158 332 A1 | 11/2001 |
| EP | 1158332 A1 | 11/2001 |
| EP | 1220190 A2 | 12/2001 |
| EP | 1 266 631 A1 | 12/2002 |
| EP | 1 271 457 A2 | 1/2003 |
| EP | 1271457 A2 | 1/2003 |
| EP | 1 652 494 A1 | 5/2006 |
| EP | 1 652 495 A1 | 5/2006 |
| EP | 1 749 545 A2 | 2/2007 |
| EP | 1 658 011 B1 | 8/2007 |
| EP | 1 867 289 A2 | 12/2007 |
| EP | 1 362 564 B1 | 11/2008 |
| EP | 0 996 370 B1 | 12/2008 |
| EP | 2 005 944 A1 | 12/2008 |
| EP | 1411839 B1 | 12/2008 |
| EP | 1 173 110 B1 | 7/2009 |
| EP | 2305141 A1 | 4/2011 |
| EP | 2314231 A1 | 4/2011 |
| GB | 2 139 898 A | 11/1984 |
| JP | 2004135905 A | 5/2004 |
| JP | 4090991 A | 3/2008 |
| JP | 4440953 B2 | 1/2010 |
| WO | WO 80/01460 A1 | 7/1980 |
| WO | WO 89/11257 A1 | 11/1989 |
| WO | WO 90/01969 A1 | 3/1990 |
| WO | WO 92/14408 A1 | 9/1992 |
| WO | WO 94/16629 A1 | 8/1994 |
| WO | WO 95/17859 A1 | 7/1995 |
| WO | WO 95/18585 A1 | 7/1995 |
| WO | WO 97/42910 A1 | 11/1997 |
| WO | WO 97/48351 A1 | 12/1997 |
| WO | WO 98/04198 A1 | 2/1998 |

(56) References Cited

FOREIGN PATENT DOCUMENTS

| | | |
|---|---|---|
| WO | WO 98/11828 A1 | 3/1998 |
| WO | WO 98/50102 A1 | 11/1998 |
| WO | WO 98/51408 A1 | 11/1998 |
| WO | WO 98/54930 A2 | 12/1998 |
| WO | WO 99/02092 A1 | 1/1999 |
| WO | WO 99/05977 A1 | 2/1999 |
| WO | WO 99/07293 A1 | 2/1999 |
| WO | WO 99/39662 A1 | 8/1999 |
| WO | WO 99/40873 A1 | 8/1999 |
| WO | WO 99/40874 A1 | 8/1999 |
| WO | WO 99/53862 A1 | 10/1999 |
| WO | WO 99/29479 A1 | 11/1999 |
| WO | WO 99/59479 A1 | 11/1999 |
| WO | WO 99/62429 A1 | 12/1999 |
| WO | WO 99/62432 A1 | 12/1999 |
| WO | WO 99/65397 A1 | 12/1999 |
| WO | WO 00/04845 A2 | 2/2000 |
| WO | WO 00/07524 A1 | 2/2000 |
| WO | WO 00/13593 A1 | 3/2000 |
| WO | WO 00/18321 A1 | 4/2000 |
| WO | WO 00/27292 A1 | 5/2000 |
| WO | WO 00/32112 A1 | 6/2000 |
| WO | WO 00/44306 A1 | 8/2000 |
| WO | WO 00/56247 A1 | 9/2000 |
| WO | WO 00/56370 A1 | 9/2000 |
| WO | WO 00/56380 A1 | 9/2000 |
| WO | WO 00/57818 A1 | 10/2000 |
| WO | WO 00/62711 A1 | 10/2000 |
| WO | WO 00/66183 A1 | 11/2000 |
| WO | WO 00/69368 A2 | 11/2000 |
| WO | WO 00/74577 A1 | 12/2000 |
| WO | WO 01/01890 A1 | 1/2001 |
| WO | WO 01/03607 A2 | 1/2001 |
| WO | WO 01/21108 A1 | 3/2001 |
| WO | WO 01/28434 A1 | 4/2001 |
| WO | WO 01/37892 A1 | 5/2001 |
| WO | WO 01/41676 A1 | 6/2001 |
| WO | WO 01/93780 A2 | 12/2001 |
| WO | WO 02/05731 A1 | 1/2002 |
| WO | WO 02/054980 A2 | 7/2002 |
| WO | WO 02/080782 A1 | 10/2002 |
| WO | WO 02/087472 A1 | 11/2002 |
| WO | WO 03/007785 A2 | 1/2003 |
| WO | WO 03/007823 A1 | 1/2003 |
| WO | WO 03/071347 A1 | 8/2003 |
| WO | WO 03/077984 A1 | 9/2003 |
| WO | WO 2004/019790 A1 | 3/2004 |
| WO | WO 00/48517 A1 | 8/2004 |
| WO | WO 2004/091381 A2 | 10/2004 |
| WO | WO 2005/037129 A2 | 4/2005 |
| WO | WO 2005/037138 A2 | 4/2005 |
| WO | WO 2005/065579 A1 | 7/2005 |
| WO | WO 2005/072196 A2 | 8/2005 |
| WO | WO 2005/072809 A1 | 8/2005 |
| WO | WO 2005/084583 A2 | 9/2005 |
| WO | WO 2005/084584 A1 | 9/2005 |
| WO | WO 2005/084585 A1 | 9/2005 |
| WO | WO 2006/022948 A1 | 3/2006 |
| WO | WO 2006/031602 A1 | 3/2006 |
| WO | WO 2006/034050 A2 | 3/2006 |
| WO | WO 2006/034114 A2 | 3/2006 |
| WO | WO 2006/034140 A2 | 3/2006 |
| WO | WO 2006/034153 A2 | 3/2006 |
| WO | WO 2006/034166 A2 | 3/2006 |
| WO | WO 2006/034301 A1 | 3/2006 |
| WO | WO 2006/037084 A1 | 4/2006 |
| WO | WO 2006/055182 A1 | 5/2006 |
| WO | WO 2006/071242 A1 | 7/2006 |
| WO | WO 2006/071243 A1 | 7/2006 |
| WO | WO 2006/071244 A1 | 7/2006 |
| WO | WO 2006/071245 A1 | 7/2006 |
| WO | WO 2006/074060 A2 | 7/2006 |
| WO | WO 2005/072196 A2 | 8/2006 |
| WO | WO 2006/081407 A1 | 8/2006 |
| WO | WO 2007/028452 A1 | 3/2007 |
| WO | WO 2007/062661 A2 | 6/2007 |
| WO | WO 2007/064819 A2 | 6/2007 |
| WO | WO 2008/074027 A1 | 6/2008 |
| WO | WO 2009/003049 A2 | 12/2008 |
| WO | WO 2009/067629 A2 | 5/2009 |
| WO | WO 2009/089216 A2 | 7/2009 |
| WO | WO 2009/089218 A2 | 7/2009 |
| WO | WO 2009/105176 A2 | 8/2009 |
| WO | WO 2009/105710 A1 | 8/2009 |
| WO | WO 2009/132141 A1 | 10/2009 |
| WO | WO 2010/062880 A1 | 6/2010 |
| WO | WO 2010/085794 A2 | 7/2010 |
| WO | WO 2010/120926 A1 | 10/2010 |
| WO | WO 2011/084536 A2 | 7/2011 |
| WO | WO 2012/087301 A1 | 6/2012 |

OTHER PUBLICATIONS

United States Patent and Trademark Office, Office Action mailed Oct. 27, 2011 in U.S. Appl. No. 12/146,252, 12 pages.

United States Patent and Trademark Office, Final Office Action mailed Oct. 29, 2010 in U.S. Appl. No. 12/146,252, 11 pages.

United States Patent and Trademark Office, Office Action mailed Apr. 22, 2010 in U.S. Appl. No. 12/146,252, 13 pages.

European Patent Office, Examination Report dated Feb. 4, 2010 in European Patent Application No. 08018517.6, 4 pages.

Chinese Patent Office, First Office Action mailed Jan. 22, 2010 in Chinese Patent Application U.S. Appl. No. 200580008634.0, 9 pages.

Japanese Patent Office, Office Action mailed Jan. 12, 2010 in U.S. Patent Application Serial No. 2006509415, 5 pages.

IP Australia, Examiner's Report mailed Nov. 12, 2009 in Australian Patent Application No. 2005208722, 2 pages.

United States Patent and Trademark Office, Office Action mailed Jul. 22, 2009 in U.S. Appl. No. 10/892,884, 7 pages.

WIPO, U.S. International Search Authority, International Search Report and Written Opinion mailed Oct. 3, 2008 in International Patent Application No. PCT/US 2008/068210, 5 pages.

European Patent Office, Supplementary European Search Report dated Jun. 10, 2008 in European Patent Application No. EP 04 75 9007, 5 pages.

WIPO, U.S. International Search Authority, International Search Report and Written Opinion mailed Jul. 30, 2007 in International Patent Application No. PCT/US2005/001621, 11 pages.

European Patent Office, Supplementary European Search Report dated Feb. 6, 2007 in European Patent Application No. EP 04 81 7975, 4 pages.

WIPO, U.S. International Search Authority, International Search Report and Written Opinion mailed Feb. 14, 2006 in International Patent Application No. PCT/US 04/09528, 7 pages.

WIPO, U.S. International Search Authority, International Search Report and Written Opinion mailed Oct. 3, 2005 in International Patent Application No. PCT/US08/68210, 4 pages.

Hayes et al., "Video-speed electronic paper based on electrowetting," *Nature*, vol. 425 Sep. 25, 2003, pp. 3 pages.

Lownie et al., "Endovascular Therapy of a Large Vertebral Artery Aneurysm using Stent and Coils," *Canadian Journal of Neurological Sciences*, vol. 27/ No. 2 May 2000, pp. 162-165.

Klee et al., "Bioactive Coating of Platinum Surfaces for Embolization Coils," *Society for Biomaterials*, 2000, 1 page.

Whitelock et al., "Perlecan coating of vascular grafts enhances endothelial cell growth," *Society for Biomaterials*, 2000, 1 page.

Hoepp et al., "Transcatheter closure of atrial-septal defects and patent foramen ovale in adults: Optimal anatomic adaptation of occlusion device," *American Heart Journal*, vol. 138/ No. 5, Nov. 1999, pp. 941-949.

Raymond et al., "Fibrinogen and Vascular Smooth Muscle Cell Grafts Promote Healing of Experimental Aneurysms Treated by Embolization," www.strokeaha.org, vol. 30, May 17, 1999, pp. 1657-1664.

Kalra et al., "Transcatheter closure of ventricular septal defect using detachable steel coil," *Heart*, vol. 82, 1999, pp. 395-396.

(56) References Cited

OTHER PUBLICATIONS

Wakhloo et al., "Stents for Intracranial Aneurysms: The Beginning of a New Endovascular Era?," *Neurosurgery*, vol. 43/ No. 2, Aug. 1998, pp. 377-379.
Vinuela et al., "Guglielmi detachable coil embolization of acute intracranial aneurysm: perioperative anatomical and clinical outcome in 403 patients," *J Neurosurg.*, vol. 86, Mar. 1997, pp. 475-482.
Post et al., "Experimental Nonsurgical Transcervical Sterilization with a Custom-Designed Platinum Microcoil," *Journal of Vascular and Interventional Radiology*, vol. 8, Jan.-Feb. 1997, pp. 113-118.
Massoud et al., "Endovascular Treatment of Fusiform Aneurysms with Stents and Coils: Technical Feasibility in a Swine Model," *AJNR AM J Neuroradiol*, vol. 16, Nov. 1995, pp. 1953-1963.
Dawson et al., "Treatment of Experimental Aneurysms Using Collagen-coated Microcoils," *Neurosurgery*, vol. 36, Jan. 1995, pp. 133-140.
Geremia et al., "Embolization of Experimentally Created Aneurysms with Intravascular Stent Devices," *AJNR*, vol. 15 Aug. 1994, pp. 1223-1231.
Szikora et al., "Combined Use of Stents and Coiils to Treat Experimental Wide-Necked Carotid Aneurysms: Preliminary Results," *AJNR Am J Neuroradiol*, vol. 15, Jun. 1994, pp. 1091-1102.
Turjman et al., "Combined Stent Implantation and Endosaccular Coil Placement for Treatment of Experimental Wide-Necked Aneurysms: A Feasibility Study in Swine," *AJNR*, vol. 18 Jun. 1994, pp. 1087-1990.
Schmitz-Rode et al., "Self-expandable spindle for transcatheter vascular occlusion: in vivo experiments," *Radiology*, Jul. 1993, pp. 95-100.
Ahuja et al., "Platinum Coil Coatings to Increase Thrombogenicity: A Preliminary Study in Rabbits," *AJNR*, vol. 14 Jul.-Aug. 1993, pp. 794-798.
Weber, "Techniques and results of therapeutic catheter embolization of congenital vascular defects," *International Angiology*, vol. 9, Jul.-Sep. 1990, pp. 214-223.
"Types of Biodegradable Hydrogels for Drug Delivery," vol. 3, published 1993, pp. 35-66.
United States Patent and Trademark Office, Office Action mailed Jun. 24, 2014 in U.S. Appl. No. 13/470,066, 8 pages.
Canadian Intellectual Property Office, Office Action mailed May 16, 2014 in Canadian Patent Application No. 2,704,920, 3 pages.
United States Patetn and Trademark Office, Final Office Action mailed Mar. 6, 2014 in U.S. Patent Application No. 13/557,068, 10 pages.
Chinese Patent Office, Final Office Action mailed Dec. 10, 2013 in Chinese Patent Application No. 200880104160.3, 6 pages.
United States Patent and Trademark Office, Office Action mailed Sep. 25, 2013 in U.S. Patent Application No. 13/557,068, 16 pages.
European Patent Office, Examination Report dated Sep. 6, 2013 in European Patent Application No. ep05711629.5, 4 pages.
United States Patent and Trademark Office, Office Action mailed Jun. 21, 2013 in U.S. Appl. No. 13/003,277, 11 pages.
Chinese Patent Office, Third Office Action mailed May 22, 2013 in Chinese Patent Application No. 200880104160.3, 9 pages.
Japan Patent Office, Office Action mailed Nov. 29, 2012 in Japanese Application No. 2010515085, 7 pages.
Chinese Patent Office, Second Office Action mailed Nov. 21, 2012 in Chinese Patent Application No. 200880104160.3, 8 pages.
European Patent Office, Examination Report dated Sep. 18, 2012 in European Patent Application No. 05711629.5, 4 pages.
Chinese Patent Office, Office Action mailed Apr. 14, 2012 in Chinese Patent Application No. 200880104160.3, 14 pages.
WIPO, U.S. International Search Authority, International Search Report and Written Opinion mailed Mar. 7, 2011 in International Patent Application No. PCT/US2010/061627, 9 pages.
European Patent Office, Supplementary European Search Report dated Mar. 2, 2011 in European Patent Application No. 10183028.9-1269, 7 pages.
European Patent Office, Examination Report dated Feb. 28, 2011 in European Patent Application No. 08018517.6-1269, 6 pages.

European Patent Office, Examination Report dated Apr. 23, 2010 in European Patent Application No. 97930198.3, 5 pages.
United States Patent and Trademark Office, Office Action mailed Mar. 3, 2010 in U.S. Appl. No. 11/107,600, 7 pages.
Japan Patent Office, Office Action mailed Jan. 12, 2010 in Japanese Patent Application No. JP2006-509415, 5 pages.
United States Patent and Trademark Office, Final Office Action mailed Aug. 26, 2009 in U.S. Appl. No. 11/107,600, 5 pages.
United States Patent and Trademark Office, Final Office Action mailed Mar. 5, 2009 in U.S. Appl. No. 10/726,135, 16 pages.
United States Patent and Trademark Office, Office Action mailed Mar. 3, 2009 in U.S. Appl. No. 11/678,544, 7 pages.
United States Patent and Trademark Office, Office Action mailed Feb. 20, 2009 in U.S. Appl. No. 11/107,600, 17 pages.
European Patent Office, Supplementary European Search Report dated Dec. 4, 2008 in European Patent Application No. 05711629.5-2310, 3 pages.
WIPO, U.S. International Search Authority, International Search Report and Written Opinion mailed Oct. 3, 2008 in International Patent Application No. PCT/US2008/068210, 9 pages.
European Patent Office, Supplementary European Search Report dated Jun. 10, 2008 in European Patent Application No. EP04759007, 5 pages.
United States Patent and Trademark Office, Office Action mailed Feb. 5, 2008 in U.S. Appl. No. 10/726,135, 13 pages.
Chinese Patent Office, Fourth Office Action mailed Aug. 24, 2007 in Chinese Patent Application No. 02815814.5, 8 pages.
WIPO, U.S. International Search Authority, International Search Report and Written Opinion mailed Jul. 30, 2007 in International Patent Application No. PCT/US05/01621, 11 pages.
Chinese Patent Office, Third Office Action mailed Feb. 9, 2007 in Chinese Patent Application No. 02818514.5, 4 pages.
European Patent Office, Supplementary European Search Report dated Feb. 6, 2007 in European Patent Application No. EP04817975, 4 pages.
United States Patent and Trademark Office, Office Action mailed Jan. 4, 2007 in U.S. Appl. No. 10/726,135, 6 pages.
United States Patent and Trademark Office, Final Office Action mailed Aug. 23, 2006 in U.S. Appl. No. 10/400,138, 6 pages.
European Patent Office, Examination Report dated Jul. 31, 2006 in European Patent Application No. EP 02 748 152.2, 8 pages.
European Patent Office, Examination Report dated Apr. 18, 2006 in European Patent Application No. 97 930 198.3, 5 pages.
WIPO, International Search Authority, Written Report mailed Feb. 14, 2006 in International Patent Application No. PCT/US04/09528, 3 pages.
WIPO, U.S. International Search Authority, International Search Report and Written Opinion mailed Feb. 14, 2006 in International Patent Application No. PCT/US04/09528, 7 pages.
WIPO, International Search Authority, International Search Report mailed Feb. 14, 2006 in International Patent Application No. PCT/US04/09528, 7 pages.
United States Patent and Trademark Office, Office Action mailed Dec. 14, 2005 in U.S. Appl. No. 10/400,138, 7 pages.
European Patent Office, Supplementary European Search Repot dated Sep. 30, 2005, in European Patent Application No. EP02748152, 4 pages.
WIPO, U.S. International Preliminary Examining Authority, International Preliminary Examination Report in International Patent Application No. PCT/US2002/022242 mailed Oct. 8, 2004, 6 pages.
United States Patent and Trademark Office, Final Office Action mailed May 19, 2005 in U.S. Appl. No. 10/400,138, 7 pages.
United States Patent and Trademark Office, Final Office Action mailed Dec. 15, 2004 in U.S. Appl. No. 09/758,832, 9 pages.
United States Patent and Trademark Office, Office Action mailed Nov. 17, 2004 in U.S. Appl. No. 10/400,138, 7 pages.
WIPO, U.S. International Search Authority, Written Opinion mailed Apr. 9, 2004 in International Patent Application No. PCT/US2002/022242, 2 pages.
WIPO, U.S. International Search Authority, International Search Report mailed Dec. 5, 2003 in International Patent Application No. PCT/US02/22242, 7 pages.

(56) References Cited

OTHER PUBLICATIONS

United States Patent and Trademark Office, Office Action mailed Nov. 18, 2003 in U.S. Appl. No. 09/758,832, 12 pages.
Hayes, R.A., "Video-speed electronic paper based on electrowetting," Nature, vol. 425, Nature Publishing Group, Sep. 25, 2003, 3pages.
United States Patent and Trademark Office, Final Office Action mailed Jun. 23, 2003 in U.S. Appl. No. 09/758,832, 9 pages.
United States Patent and Trademark Office, Office Action mailed Feb. 27, 2003 in U.S. Patent Application 09/906,415, 11 pages.
United States Patent and Trademark Office, Office Action mailed Dec. 16, 2002 in U.S. Appl. No. 09/758,832, 6 pages.
United States Patent and Trademark Office, Final Office Action mailed Oct. 8, 2002 in U.S. Appl. No. 09/758,832, 7 pages.
United States Patent and Trademark Office, Office Action mailed Jul. 16, 2002 in U.S. Appl. No. 09/758,832, 16 pages.
WIPO, U.S. International Search Authority, International Search Report mailed Nov. 6, 1997 in International Patent Application No. PCT/US97/10882, 4 pages.
Guglielmi, G. et al., "Electrotrombosis of saccular aneurysms via endovascular approach", J. Neurosurg.1991; 75; 8-14.
Paper No. 199, American Society of Neuroradiology, 29$^{th}$ Annual Meeting Washington, D.C., Jun. 9-14, 1991.
Paper No. 200, American society of Neuroradiology, 29$^{th}$ Annual Meeting Washington, D.C., Jun. 9-14, 1991.
Strecker E.P., "Flexible, Balloon Expandable Percutaneously Insertable Vascular Prosthesis: Experimental and Clinical Results", Radiology 1988; 169 :388.
Sigward, V. et al., "Intravascular Stents to Prevent Occlusion and Restenosis After Transluminal Angioplasty" N. England J. Med., 1987; 316:701-706.
Duprat, G. Jr., et al. "Self expanding Metallic Stents for Small Vessels: An Experimental Evaluation", Radiology 1987;162: 469-472.
Romodanov, A.P. et al., "Intravascular Occlusion Catheter", In Advances &Technical Standards, vol. 9, 1982; 25-49.
Hieshima, G.B. et al., "A Detachable Balloon for Therapeutic Transcatheter Occlusions", Radiology 1981; 138; 227-228.
Zollikofer M.D., C., "A Combination of Stainless Steel Coil and Compressed Ivalon: A New Technique for Embolization of Large Arteries and Arteriovenous Fistulas," Radiology 138:229-231, Jan. 1, 1981, 3 pages.
Serbinenko, F.A "Balloon Catherization and Cerebral Vessels", J. Neurosurg. 1974; 41: 125-145.

* cited by examiner

SELF-EXPANDING PROSTHESIS

RELATED APPLICATIONS

The present application claims benefit of U.S. Provisional Application Ser. No. 60/946,101, filed Jun. 25, 2007 entitled Self-Expanding Prosthesis; which is incorporated herein by reference.

BACKGROUND OF THE INVENTION

Endoprosthesis devices, more generally referred to as stents, are known in the art for treating a wide range of medical conditions. Generally, an endoprosthesis consists of a cylindrical device that can be expanded from a smaller diameter configuration to a larger diameter configuration. The smaller diameter configuration facilitates advancing the endoprosthesis through an often convoluted lumen of a patient while the expanded diameter configuration presses against the walls of the patient's lumen, often to both anchor the prosthesis and restore the patency of the lumen.

Many endoprosthesis devices can be classified according to their method of expansion. Some devices are expanded by the exertion of an outwardly directed radial force on an inner surface of the endoprosthesis. For example, the endoprosthesis may be compressed or crimped over a deflated balloon of a balloon catheter. When the endoprosthesis is positioned at a desired target area, the balloon is inflated, expanding the endoprosthesis.

Other endoprosthesis devices are self-expanding and therefore recover to an expanded position after being compressed. For example, some self-expanding endoprosthesis devices are composed of a shape memory material such as Nitinol (Ni—Tl alloy). The shape memory material allows the device to be compressed within a delivery catheter, yet expand in diameter when released within the lumen of a patient, similar to a spring. For some applications, self-expanding endoprosthesis devices are thought to be superior to balloon expandable devices since self-expanding devices often require less elaborate delivery mechanisms (e.g., no inflatable balloons) and are often less likely to be damaged after deployment (e.g., by being crushed or otherwise permanently deformed). Examples of prior art shape memory device can be seen in U.S. Pat. No. 4,665,905 to Jervis and U.S. Pat. No. 4,925,445 to Sakamoto et al., the contents of which are hereby incorporated by reference.

However, delivery systems for self-expanding endoprosthesis devices are not without their drawbacks. For example, one common delivery system includes a catheter having a retractable sheath. The endoprosthesis device is preloaded onto a reduced diameter region on a distal end of the catheter. The retractable sheath is positioned over the device, preventing it from expanding in diameter. When a desired target location is reached by the device, the user retracts the outer sheath, releasing the self-expanding device. However, the self-expanding force can cause the device to spring laterally out of the sheath, sometimes missing the desired target area. Further, the device may tend to become imbedded within the wall of the sheath, resulting in damage to the device or the device becoming stuck. Additional delivery system details can be found in U.S. Pat. Nos. 4,580,568 and 4,732,152, the contents of which are hereby incorporated by reference.

Accordingly, there is a need for a self-expanding endoprosthesis delivery system which overcomes the disadvantages of the prior art.

OBJECTS AND SUMMARY OF THE INVENTION

It is an object of the present invention to overcome the disadvantages of the prior art.

It is another object of the present invention to provide a prosthesis delivery system that can more predictably release a prosthesis within a patient.

It is another object of the present invention to provide a prosthesis delivery system that reduces unwanted complications during delivery of the prosthesis within the patient.

The present invention seeks to achieve these objects by providing a prosthesis that can be selectively expanded. In one preferred embodiment, the prosthesis is composed of a shape memory material that expands when heated to a temperature greater than an average body temperature. When a heater positioned inside of the prosthesis is activated, the shape memory material of the prosthesis expands to a predetermined shape.

In another preferred embodiment, electrical current is directly supplied to the prosthesis with electrical leads, causing the body of the prosthesis itself to heat up and thereby expand in diameter. Once expanded, the electrical leads are detached from the prosthesis and removed from the patient.

DETAILED DESCRIPTION OF THE INVENTION

Figure 1:
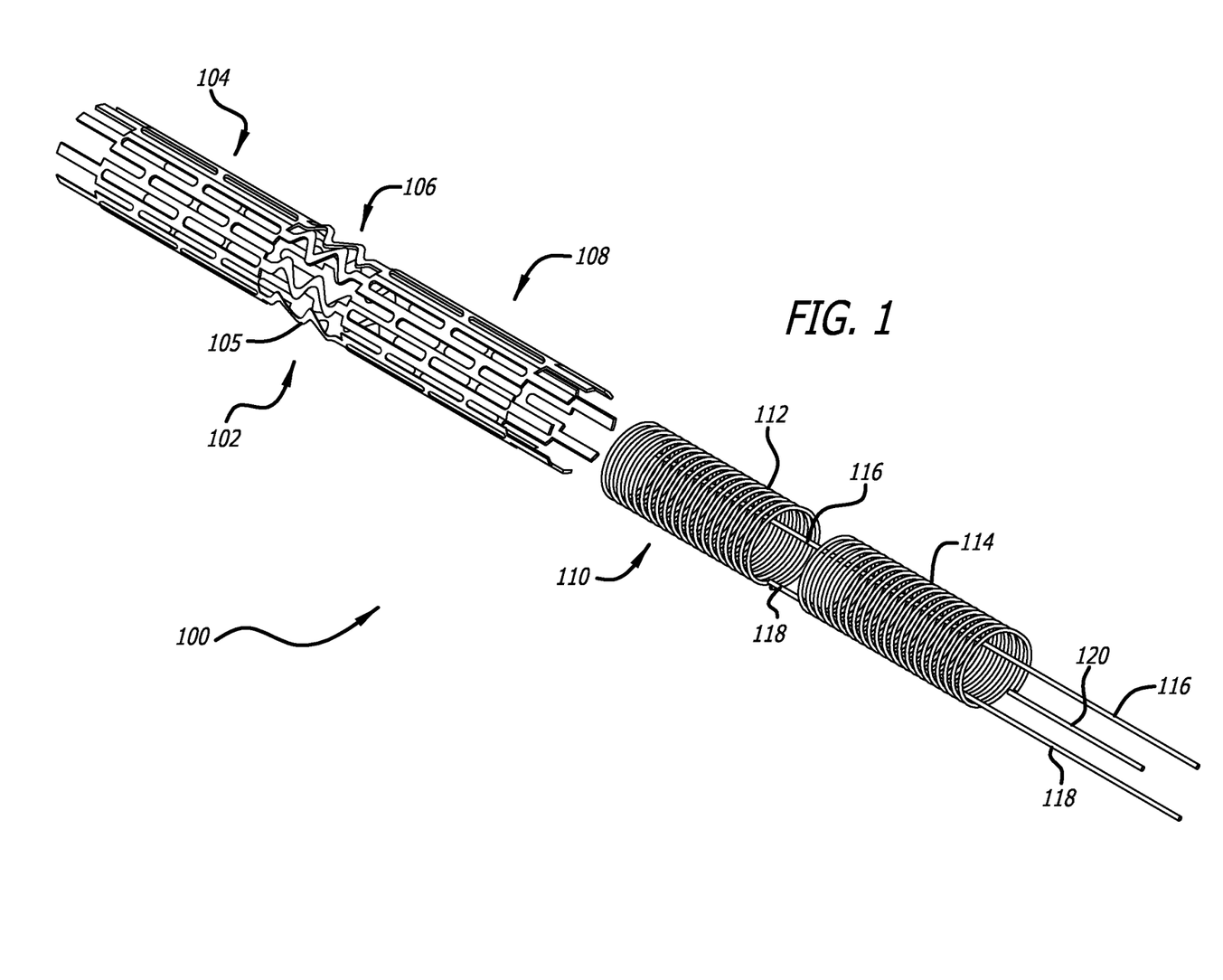
FIG. 1 illustrates a disassembled perspective view of a prosthesis deployment system according to a preferred embodiment of the present invention.
Figure 2:
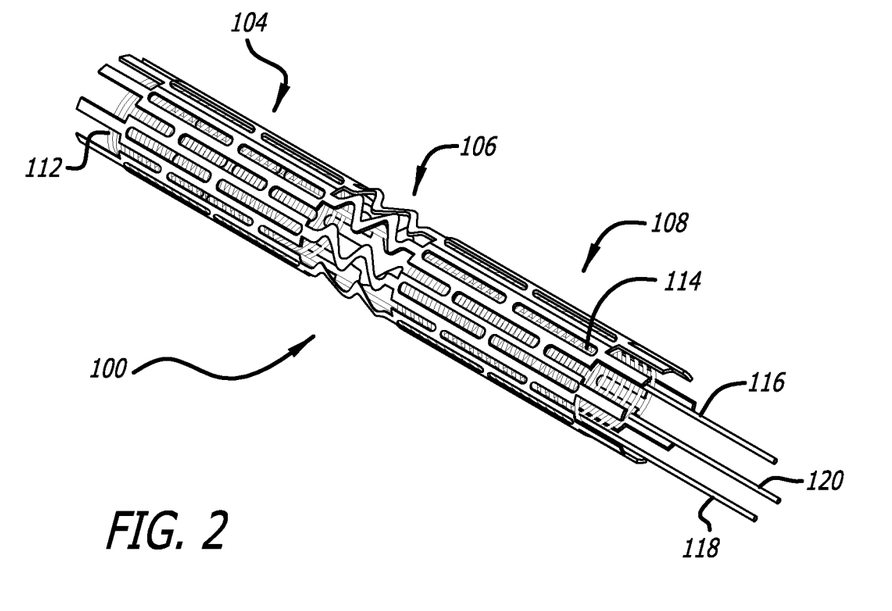
FIG. 2 illustrates an assembled perspective view of the prosthesis deployment system of FIG. 1.

Referring to FIGS. 1 and 2, a prosthesis deployment system 100 is shown according to a preferred embodiment of the present invention. This deployment system 100 includes a prosthesis 102 (e.g., a stent) which can be selectively expanded within a lumen of a patient by activating a heater 110. Due to its composition, the prosthesis 102 expands in diameter when heated to a predetermined temperature and remains expanded at the patient's body temperature. In this respect, the deployment system 100 allows a user to determine when the prosthesis 102 expands in diameter within the patient.

Preferably, the prosthesis 102 is composed of a shape memory material, such as Nitinol, which changes phases from a Martensitic state to an Austenitic state. In the Martensitic state, the prosthesis 102 maintains ductile properties which can be especially useful when delivering the prosthesis 102 through tortuous vessels within a patient. In the Austenitic state, the prosthesis 102 expands in diameter to a larger predetermined shape while becoming more rigid.

Figure 4:
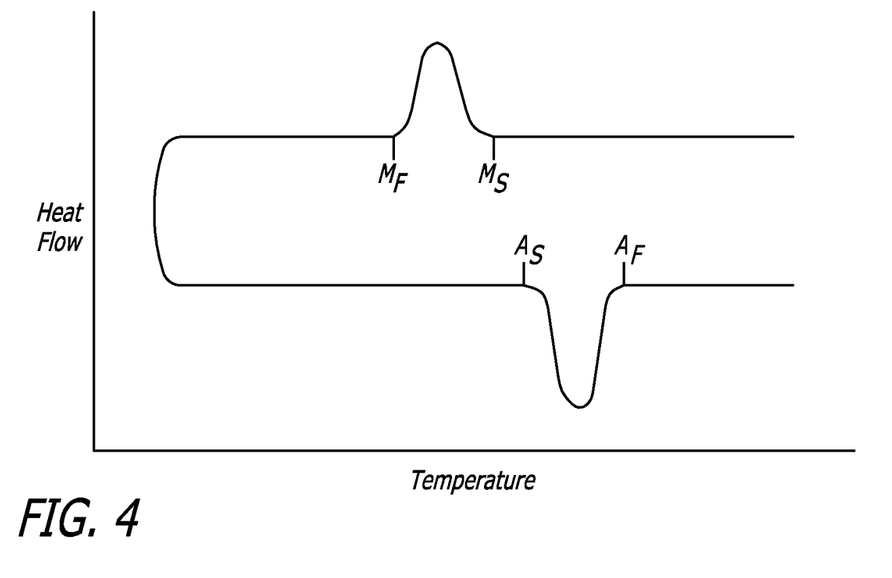
FIG. 4 illustrates a differential scanning calorimetry (DSC) graph of an example shape memory material according to a preferred embodiment of the present invention.

Referring to FIG. 4, a differential scanning calorimetry (DSC) graph is shown of an example shape memory material. The transformation temperature range from the Martensitic state of the shape memory material to the Austenitic state begins with the Active Austenite Start Temperature ($A_S$) and completes with the Active Austenite Finish Temperature ($A_F$). Similarly, the transformation temperature range from the Austenitic state to the Martensitic state begins with the Active Martensite Start Temperature ($M_S$) and completes with the Active Martensite Finish Temperature ($M_F$). As seen in the Figure, the Austenitic temperature range is generally higher than the Martensitic temperature range.

Typical self expanding stents of the prior art have an $A_F$ of 37° C. or less to ensure that the stent expands when delivered to a desired target location within the patient. However, the prosthesis of a preferred embodiment according to the present invention has an $A_S$ and $A_F$ above 37° C. while the $M_F$ and the $M_S$ remain below this temperature. Thus, the prosthesis 102 can be delivered to a target location in its flexible Martensite state, heated to transition to its expanded Austenite state (e.g., a preset shape having a larger diameter), then allowed to cool to 37° C. where the prosthesis remains in its expanded Austenite state. In other words, the prosthesis 102 can be selectively expanded by simply heating.

The desired transition temperatures can, for example, be obtained from either the Ingot Active temperature or via heat treatment.

Preferably, the $A_F$ is above 37° C. and more preferably is within the range of about 40° C. and about 55° C. For example, the $A_S$ of the prosthesis material is about 45° C. and the $A_F$ is about 55° C.

As best seen in the disassembled view of FIG. 1, the delivery system 100 includes a heater 110 which is composed of a highly resistive material which produces heat when current is passed through it. FIG. 2 illustrates an assembled view of the heater 110 positioned inside of the unexpanded prosthesis 100. When the prosthesis 102 is positioned at a desired target location within a patient, the user applies current to the heater 110, causing the heater 110 and therefore the prosthesis 102 to increase in temperature. As the prosthesis 102 reaches its $A_F$ temperature, the prosthesis 102 expands in diameter against the walls of the patient's lumen. Thus, the user can first position the prosthesis 102 at a desired location in the lumen, and then cause the prosthesis 102 to expand. Further, if the user is unsatisfied with the initial position of the prosthesis 102, it may be recaptured prior to expansion and redeployed at a more desirable location.

In the present preferred embodiment, the prosthesis 102 includes a first section 104 and a second section 108 connected by an intermediate section 106. While the first and second sections 104 and 108 are preferably composed of axially and radially interconnecting segments, the intermediate section 106 includes only axially arranged members 105 which allow each section 104 and 108 to expand independently of the other. Preferably the intermediate section 106 is unitary with and therefore the same material as the first and second sections 104 and 108. However, the intermediate section 106 may also be composed of a different material, such as a polymer, to further facilitate independent expansion of the two sections 104 and 108.

The heater 110 has matching segments in the form of a first heating coil 112 and a second heating coil 114 that are positioned within sections 104 and 108 respectively. Wires 116 and 118 supply current to the first heating coil 112 while wires 120 and 118 (electrically connected to both coils 112 and 114) provide current to the second heating coil 114. Thus, each coil 112 and 114 can be heated independently of the other which ultimately allows each section 104 and 108 of the prosthesis 102 to be expanded independently of each other. Further discussion of a similar heating mechanism can be found in U.S. Publication Number 2006/0052815, the contents of which are hereby incorporated by reference.

Preferably, the heater 110 is provided with enough current to reach a temperature equal to or greater than the transition temperature of the shape memory material of the prosthesis 102. However, it is also preferred that the max temperature and duration of heat be limited so as to prevent or minimize further damage to the patient's lumen. Additionally, the prosthesis 102 may be covered with a thin film such as a heat shrink tubing as to limit the heat exposure to the patient's lumen.

The independent expansion of sections 104 and 108 of the prosthesis 102 may allow the user to more precisely position the prosthesis 102 at a target location within a patient. For example, once the prosthesis is located at a desired target location, the user may first expand the distal first section 104 to provide an initial anchor point, and then expand the proximal second section 108. Since many prior art self expanding stents tend to shrink in length as they increase in diameter, their final position can be difficult to predict during the delivery. However, by expanding one section 104 or 108 first, the ultimate expanded position of the prosthesis 102 can be deployed to a more predictable position.

While only two sections 104 and 108 are illustrated in the present preferred embodiment, additional sections are also possible. For example, the prosthesis 102 may have 3 or 4 sections and an equal number of corresponding coils for heating each section of the prosthesis 102.

In operation, the prosthesis deployment system 100 is used to deploy the prosthesis 102 by initially passing a guidewire into the patient so that a distal end of the guidewire is positioned at a target area. A catheter or microcatheter containing both the heater 110 and the prosthesis 102 is slid over the guidewire until a distal end of the catheter reaches the desired target area of the patient's lumen. Since the prosthesis 102 is in its martensitic state, it remains relatively flexible and therefore can easily pass through tortuous passageways to reach the target area.

Once the distal end of the catheter reaches the target area, an outer sheath (if present) is retracted to expose the prosthesis 102. If the user is unsatisfied with the position of the prosthesis 102, the prosthesis 102 can optionally be recaptured by the outer sheath (again, if present) and advanced or retracted until a desired position has been achieved. The user then expands the distal first section 104 of the prosthesis 102 by causing the first heater coil 112 to increase in temperature and thereby changing the phase of the first section 104 from Martensitic to Austensitic (i.e. causing the first section 104 to move to its predetermined expanded configuration). Next, the user expands the proximal second section 108 by causing the second heater coil 114 to increase in temperature, thereby changing the phase of the second section 108. Finally, the user may confirm the final position of the prosthesis 102 (e.g., by radio fluoroscopy) and remove the catheter. In some cases, the user may prefer not to expand the proximal second section 108.

Figure 3:
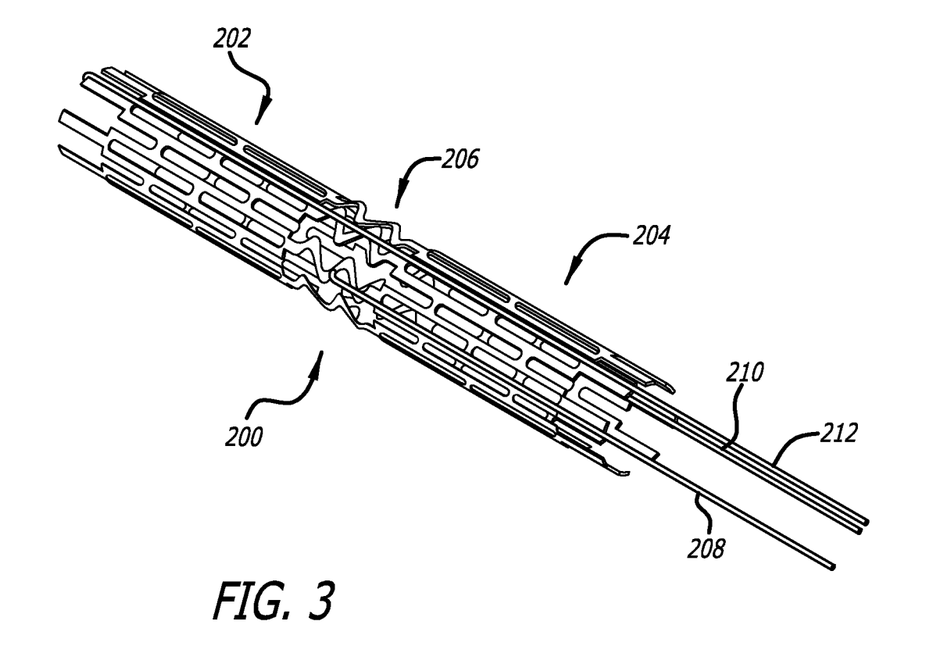
FIG. 3 illustrates a perspective view of a prosthesis deployment system according to another preferred embodiment of the present invention.

Referring now to FIG. 3, another preferred embodiment of a self-heating prosthesis 200 is illustrated according to the present. The self-heating prosthesis 200 is similar to the previously described prosthesis 102, having a first section 202 and a second section 204 connected by an intermediate section 206 which facilitates each of the sections 202 and 204 to expand independently of each other.

However, the self-heating prosthesis 200 is directly connected to wires 208, 210 and 212, which selectively provide current to increase the temperature of the prosthesis 200. More specifically, wire 212 is connected to a distal end of the first section 202 while wire 208 is connected to the intermediate section 206. When a current passes through these wires 212 and 208, it also passes through the first section 202, thereby increasing its temperature. In this respect, the prosthesis itself acts as a heating element, similar to the previously described heater coils. As with the previously described prosthesis 102, when the first section 202 passes the $A_S$ temperature it begins to expand until it reaches the $A_F$ temperature.

Additionally, a wire 210 is connected to a proximal end of the second section 204 which allows current to selectively flow between wires 210 and 208, passing through the second section 204. Thus, the temperature of the second section 204 similarly increases, ultimately causing it to pass into an expanded Austenite state. In this respect, the user can control which of the sections 202 or 204 increase in temperature and therefore expand by passing current through either wires 212 and 208 or 210 and 208.

After both sections 202 and 204 have been expanded, the wires 208, 210 and 212 are disconnected from the prosthesis 200. For example, these wires 208, 210 and 212 may have a heat sensitive connection which becomes disconnected when heated to a predetermined temperature. Alternately, the wires 208, 210 and 212 may have hooks or latching mechanisms that allow selective disconnection and removal by the user.

While electrical current is preferably used to generate heat and therefore expand the prosthesis according to the present invention, other forms of energy may also be used. For example, RF current may be used. In another example hot liquid may be delivered to the prosthesis. In yet another example, a heat-generating chemical reaction may be used.

It should be understood that the present invention, including the previously described preferred embodiments, can be used for a variety of treatments, techniques and procedures within a patient's body.

Figure 5:
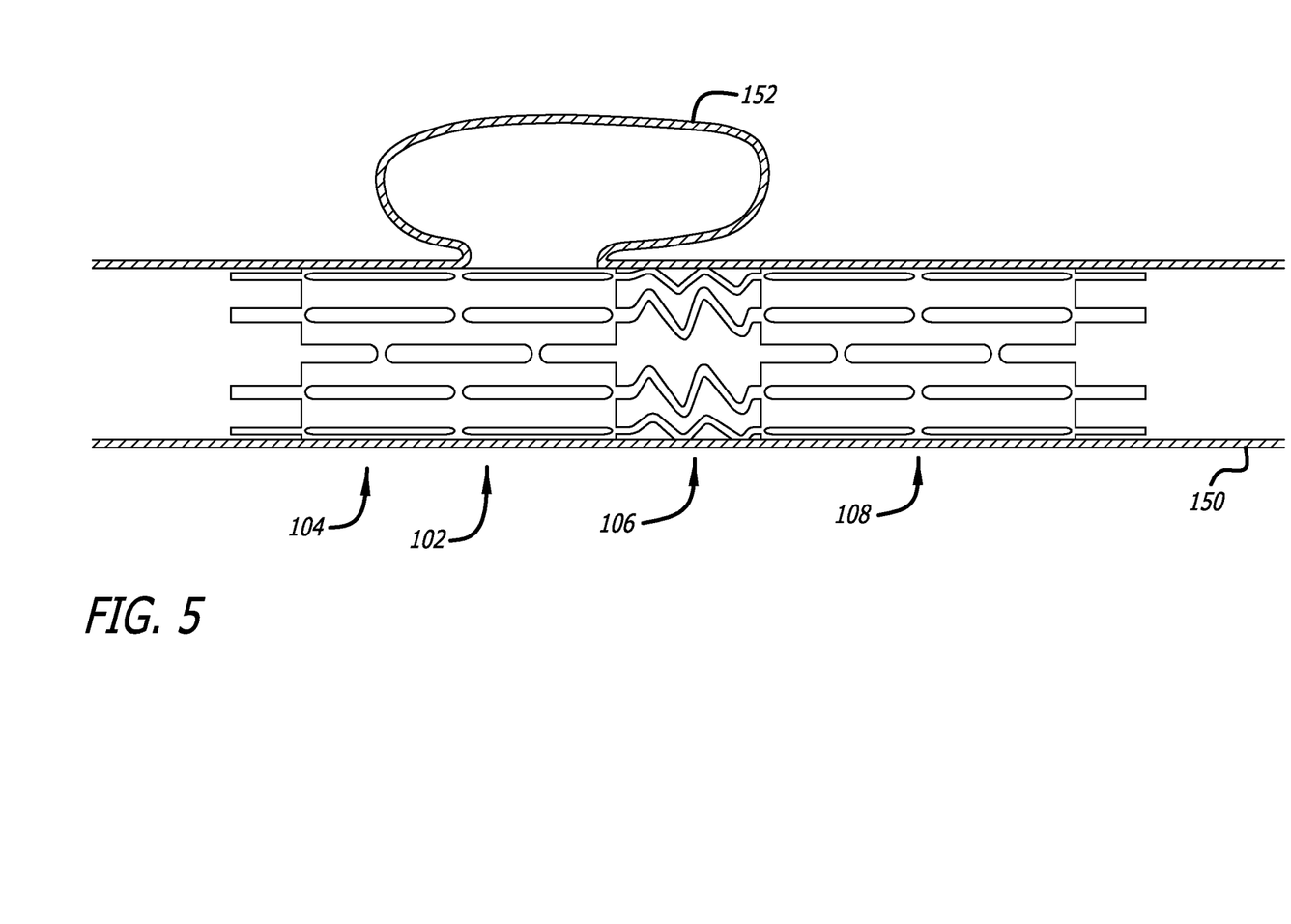
FIG. 5 illustrates a side view of the prosthesis of FIG. 1 for use in treating an aneurysm.

FIG. 5 illustrates one such example treatment for an aneurysm 152 in which the prosthesis 102 is positioned over the opening of the aneurysm 152 in a vessel 150. Once in place, tissue growth of endothelial cells is promoted (e.g., either with the prosthesis 102 alone or with tissue growth promoting agents) which ultimately results in a layer of tissue that closes of the aneurysm 152.

Figure 6:
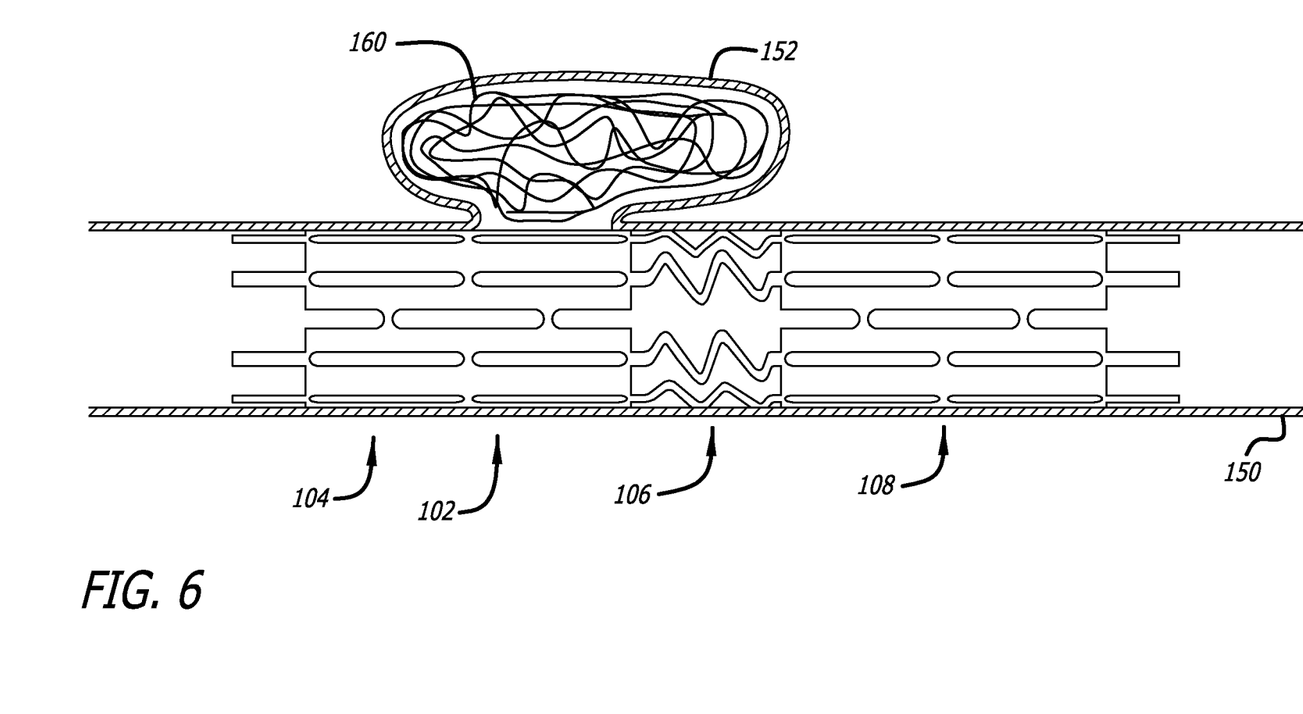
FIG. 6 illustrates a side view of the prosthesis of FIG. 1 with a prosthesis coil for use in treating an aneurysm.

FIG. 6 illustrates a similar example in which an aneurysm 152 is treated with both a prosthetic coil 160 and the prosthesis 102. More specifically, the prosthetic coil 160 is delivered into the aneurysm 152 while the prosthesis 102 is delivered over the opening of the aneurysm 152 to prevent the prosthetic coil 160 from moving into the vessel 150. Additional details regarding the use of the prosthetic coil can be found in the previously incorporated U.S. Publication Number 2006/0052815.

One preferred embodiment according to the present invention includes a method of expanding a prosthesis within a body comprising providing a prosthesis comprising a shape memory material; delivering the prosthesis to a desired location within a body; increasing a temperature of the prosthesis above a human body temperature to change a phase of the shape memory material, thereby expanding the prosthesis to an expanded state; decreasing the temperature of the prosthesis to the human body temperature while maintaining the expanded state.

In a further example of this preferred embodiment, the expanding the prosthesis further comprises expanding a diameter of the prosthesis.

In a further example of this preferred embodiment, the increasing a temperature further comprises changing the phase of the shape memory material from a martensitic state to an austenitic state.

In a further example of this preferred embodiment, the expanding the prosthesis to an expanded state further comprising: expanding a first segment of the prosthesis; and expanding a second segment of the prosthesis.

In a further example of this preferred embodiment, the expanding the prosthesis further comprises producing heat adjacent to the prosthesis.

In a further example of this preferred embodiment, the expanding the prosthesis further comprises producing heat with the prosthesis.

In a further example of this preferred embodiment, the delivering the prosthesis to a desired location within a body further comprises: locating an aneurysm; and positioning the prosthesis over an opening of the prosthesis.

In a further example of this preferred embodiment, providing a prosthesis comprising a shape memory material is followed by delivering a prosthetic coil within the aneurysm.

Another preferred embodiment according to the present invention includes a prosthesis for deploying within a human body comprising a prosthesis body having a first predetermined shape while in a first phase and a second predetermined shape while in a second phase; wherein a transition from the first phase to the second phase occurs at a temperature above a human body temperature and wherein a transition from the second phase to the first phase occurs at a temperature below the human body temperature.

In a further example of this preferred embodiment, the prosthesis body comprises a shape memory material.

In a further example of this preferred embodiment, the first phase is an austenitic state and the second state is a martensitic state.

In a further example of this preferred embodiment, the prosthesis includes an active austenite start temperature and an active austenite finish temperature above 37° C.

In a further example of this preferred embodiment, the active austenite finish temperature is within a range of about 40° C. and about 55° C.

In a further example of this preferred embodiment, the prosthesis body further comprises a first segment and a second segment wherein the first segment is independently expandable relative to the second segment.

In a further example of this preferred embodiment, the prosthesis comprises a tubular shape having an interior diameter; the diameter having a first length during the first predetermined shape and a second, increased length during the second predetermined shape.

Another preferred embodiment according to the present invention includes a prosthesis delivery system comprising a delivery tool shaped to enter a body; and a prosthesis removably disposed on the delivery tool; the prosthesis including a first shape-memory configuration and a second shape-memory configuration; the prosthesis transitioning from the first shape-memory configuration to the second shape-memory configuration at a temperature above about 37° C.; wherein the delivery tool selectively heats the prosthesis within the body.

A further example of this preferred embodiment comprises at least one heating element disposed on the delivery tool.

In a further example of this preferred embodiment, the delivery tool selectively delivers electrical current to the prosthesis.

In a further example of this preferred embodiment, the prosthesis further comprises a plurality of independently expandable regions and wherein the delivery tool further comprises a plurality of individually actuable heaters.

In a further example of this preferred embodiment, each of the plurality of independently expandable regions is disposed over a corresponding heater of the plurality of individually actuable heaters.

In another example of a preferred embodiment of the present invention, the prosthesis is tubular. More specifically, the prosthesis material is made from a laser-cut tube or is a tube formed by braided fibers or members.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of expanding a prosthesis within a body comprising:
    delivering a prosthesis formed of a shape memory material to a desired location within a body, the prosthesis having a first tubular portion and a second tubular portion connected to one another by an intermediate portion having a plurality of axially arranged members, the intermediate portion formed unitary with the first and second tubular portions;
    passing a current directly through the shape memory material of the first tubular portion and the intermediate portion such that the first tubular portion acts as a heating element and a temperature of the first tubular portion independently increases to a temperature above a human body temperature to change a phase of the shape memory material, thereby radially expanding said first tubular portion from a reduced diameter delivery state to an expanded state;
    passing a current directly through the shape memory material of the second tubular portion and the intermediate portion such that the second tubular portion acts as a heating element and a temperature of the second tubular portion independently increases to a temperature above a human body temperature to change the phase of the shape memory material, thereby radially expanding said second tubular portion from a reduced diameter delivery state to an expanded state; and
    decreasing said temperatures of the first and second tubular portions to the human body temperature while maintaining said expanded states.

2. The method of claim 1, wherein said step of passing a current directly through the shape memory material of the first tubular portion and the intermediate portion comprises changing the phase of the shape memory material of the first tubular portion from a martensitic state to an austenitic state.

3. The method of claim 1, wherein said step of passing a current directly through the shape memory material of the first tubular portion and the intermediate portion is performed before said step of passing a current directly through the shape memory material of the second tubular portion and the intermediate portion.

4. The method of claim 1 wherein the steps of passing a current comprise independently providing the current to each of said first and second tubular portions.

5. The method of claim 1, wherein said step of delivering a prosthesis formed of a shape memory material to a desired location within a body further comprises:
    locating an aneurysm; and
    positioning said prosthesis over an opening of said aneurysm.

6. The method of claim 5 further comprises delivering a prosthetic coil within said aneurysm.

7. A prosthesis delivery system comprising:
    a delivery tool shaped to enter a body;
    a prosthesis removably disposed on said delivery tool, the prosthesis comprising a pair of independently radially expandable tubular regions;
    a first tubular region and a second tubular region of said pair of independently radially expandable tubular regions connected to one another by an intermediate region having a plurality of axially arranged members, the intermediate region formed unitary with said first and second tubular region of said pair of independently radially expandable tubular regions;
    the first tubular region of said pair of independently radially expandable tubular regions and the intermediate region forming a portion of a first independent electrical circuit through which a current passes so as to heat said first tubular region independently of the second tubular region;
    the second tubular region of said pair of independently radially expandable tubular regions and the intermediate region forming a portion of a second independent electrical circuit through which a current passes so as to heat said second tubular region independently of the first tubular region;
    each of the first and second tubular regions of the pair of independently radially expandable tubular regions configured to remain in a Martensite phase having a delivery diameter after exposure to a target area and to transition to an Austenite phase having an expanded diameter larger than the delivery diameter after heating to a temperature above 37 degrees Celsius.

8. The prosthesis delivery system of claim 7, wherein said first independent electrical circuit further comprises a first wire directly connected to said first tubular region and a second wire directly connected to said intermediate region.

9. The prosthesis delivery system of claim 7 wherein the first tubular region of said pair of independently radially expandable regions transitions from said Martensite phase to said Austenite phase before a second of said pair of independently radially expandable regions transitions from said Martensite phase to said Austenite phase.

* * * * *